(12) United States Patent
Miyazaki et al.

(10) Patent No.: US 6,407,251 B1
(45) Date of Patent: Jun. 18, 2002

(54) PROCESS FOR PREPARING 2-CHLORO-5-CHLOROMETHYLTHIAZOLE

(75) Inventors: Takashi Miyazaki; Makoto Satou; Yoshihisa Inoue, all of Hikari (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 10/004,829

(22) Filed: Dec. 7, 2001

(30) Foreign Application Priority Data

Dec. 28, 2000 (JP) ........................................ 2000-400802

(51) Int. Cl.$^7$ ............................................. C07D 277/20
(52) U.S. Cl. ...................................................... 548/202
(58) Field of Search ......................................... 548/202

(56) References Cited

U.S. PATENT DOCUMENTS 4,748,243 A    5/1988  Beck et al. .................. 548/202

FOREIGN PATENT DOCUMENTS

| EP | 0 376 279      | 7/1990 |
| EP | 0 794 180      | 9/1997 |
| EP | 1 031 566      | 8/2000 |
| EP | 1 031 566 A1 * | 8/2000 |
| JP | 3-157308       | 7/1991 |
| JP | 4-234864       | 8/1992 |
| JP | 9-136874       | 5/1997 |
| WO | 97/10226       | 3/1997 |

OTHER PUBLICATIONS

H. Uneme et al., "Synthesis and insecticidal activity of nitro–guanidine derivatives", Pestic. Sci., vol. 55, pp. 197–218, 1999.

T. Gobel et al., "Synthetic approaches towards CGA 293'343: A novel broad–spectrum insecticide", Pestic. Sci., vol. 55, pp. 355–357, 1999.

Chemical Society Japan, the $77^{th}$ autumn annual meeting abstract, p. 424 with its English translation.

* cited by examiner

*Primary Examiner*—Joseph K. McKane
*Assistant Examiner*—Rebecca Anderson
(74) *Attorney, Agent, or Firm*—Wenderoth, Lind & Ponack, L.L.P.

(57) ABSTRACT

A novel process for preparing 2-chloro-5-chloromethylthiazole is provided which is suitable for industrial application.

The process for preparing 2-chloro-5-chloromethylthiazole involves allowing 2-halogenoallyl isothiocyanate to react with chlorinating agent in the presence of an aromatic hydrocarbon which may have one or more substituents.

4 Claims, No Drawings

PROCESS FOR PREPARING 2-CHLORO-5-CHLOROMETHYLTHIAZOLE

BACKGROUND OF THE INVENTION

1. Field of the Invention

The present invention relates to a novel process for preparing 2-chloro-5-chloromethylthiazole.

2. Description of the Prior Art 2-chloro-5-chloromethylthiazole is an important compound as an intermediate product in a process for preparing biologically active compounds such as insecticides (see, for example, Japanese Patent Application Laid-Open No. 3-157308 (1991)) It can be prepared by, for example, the following processes.

Japanese Patent Application Laid-Open No.63-83079 (1988) discloses a process for preparing 2-chloro-5-chloromethylthiazole by allowing allyl isothiocyanate to react with chlorinating agent as described in the following scheme (A):

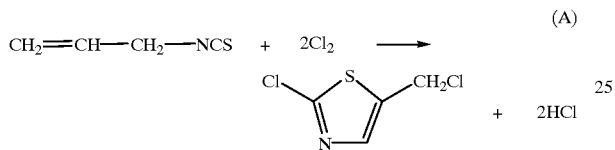

(A)

This process requires a large amount of chlorinating agent and the reaction has to be performed under a high temperature, which produces many by-products. Therefore, it is not so suitable for industrial application.

Alternatively, Japanese Patent Application Laid-Open No. 4-234864 discloses a process for preparing 2-chloro-5-chloromethylthiazole by allowing allyl isothiocyanate derivative to react with chlorinating agent as described in the following scheme (B):

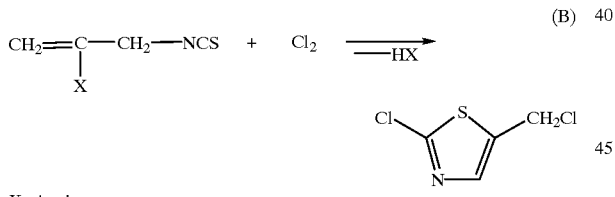

(B)

X = leaving group

This process is suitable for industrial application which can be performed using approximately an equal amount of chlorinating agent under moderate condition to give a high yield. However, inert solvent (diluent) such as halocarbon may preferably be used to give a high yield, which requires high production cost.

Japanese Patent Application Laid-Open No. 2000-247963 (2000) discloses a process which involves allowing 2-halogenoallyl isothiocyanate to react with chlorinating agent in a dipolar aprotic solvent such as acetonitrile. This process, however, has a disadvantage that the solvent cannot be reused since it is difficult to separate and collect the solvent such as acetonitrile from water.

Accordingly, a novel process for preparing 2-chloro-5-chloromethylthiazole suitable for industrial application is still needed in which an excess amount of chlorinating agent is not required, moderate conditions can be used to give a high yield, and solvent can be collected easily.

The object of the present invention to provide a novel process for preparing 2-chloro-5-chloromethylthiazole which is suitable for industrial application.

SUMMARY OF THE INVENTION

Aromatic hydrocarbons and derivatives thereof (particularly toluene) are reactive with chlorinating agent. The present inventors unexpectedly found, as a result of intense studies, that 2-chloro-5-chloromethylthiazole can be obtained at a high yield by allowing 2-halogeno-allyl isothiocyanate to react with chlorinating agent in the presence of aromatic hydrocarbons which may have one or more substituents, and accomplished the present invention based on the findings.

In other words, the present invention provides:

(1) a process for preparing 2-chloro-5-chloromethylthiazole of the following formula (I):

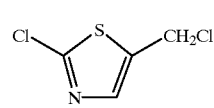

(I)

by allowing 2-halogeno-allyl isothiocyanate of the following formula (II):

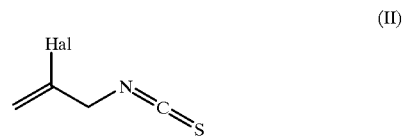

(II)

(wherein Hal represents chlorine or bromine) to react with chlorinating agent in the presence of an aromatic hydrocarbons which may have one or more substituents;

(2) the process according to (1) above wherein the aromatic hydrocarbons which may have one or more substituents is toluene, chlorobenzene or dichlorobenzene; and (3) the process according to (1) above wherein the aromatic hydrocarbons which may have one or more substituents is toluene.

(4) the process according to (1) above wherein Hal in the formula (II) is chlorine.

DETAILED DESCRIPTION OF THE INVENTION

A 2-halogenoallyl isothiocyanate of the following formula (II):

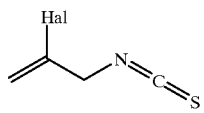

(wherein Hal represents chlorine or bromine) is a known compound which can be prepared by any known processes. One unlimiting example of such process involves heating a mixture of 2,3-dihalogeno-1-propene (e.g., 2,3-dichloro-1-propene) with thiocyanate represented by M(SCN)n (wherein M represents metal or ammonium group, and n indicates the valence of M) in the presence of water (see, Japanese Patent Application Laid-Open No. 9-136874 (1997)).

The process according to the present invention may be performed in the presence of an "aromatic hydrocarbons which may have one or more substituents". The aromatic hydrocarbon in the "aromatic hydrocarbon which may have one or more substituents" herein may include, for example, benzene, naphthalene and phenanthrene. The "aromatic hydrocarbon" may be substitutedwith, for example, $C_{1-4}$ alkyl group (e.g., methyl, ethyl, propyl, isopropyl, butyl, isobutyl, s-butyl or t-butyl) and/or halogen (e.g., fluorine, chlorine, bromine or iodine) and number of substituents is preferably 1 to 3. Examples of such "aromatic hydrocarbons which may have one or more substituents" are toluene, o-, m-, p-xylene and xylene isomeric mixtures, ethylbenzene, cumene, cymene, mesitylene, chlorobenzene, as well as o-, m- or p-dichlorobenzene and isomeric mixtures of dichlorobenzene. Preferable examples of "aromatic hydrocarbons which may have one or more substituents" are chlorobenzene, dichlorobenzene (o-, m- or p-dichlorobenzene or mixtures thereof) and toluene, among them toluene is particularly preferable. The "aromatic hydrocarbons which may have one or more substituents" may be used alone or in combination of two or more thereof.

Preferably 0.1 to 20 parts and more preferably 0.5 to 5 parts by weight of the "aromatic hydrocarbons which may have one or more substituents" may be used relative to 1 part by weight of the above-described 2-halogenoallyl isothiocyanate.

The term "chlorinating agent" herein refers to chlorine or a compound which releases chlorine under reaction conditions, such as sulfuryl chloride or phosgene. The chlorinating agent is typically used in an amount of 0.8 to 2 equivalents, preferably 1.0 to 1.5 equivalents, and more preferably 1.05 to 1.30 equivalents relative to the above-described 2-halogenoallyl isothiocyanate.

For example, a reaction process according to the present invention using 2-chloroallyl isothiocyanate as the starting material and sulfuryl chloride as the chlorinating agent can be particularly described with reference to the following scheme.

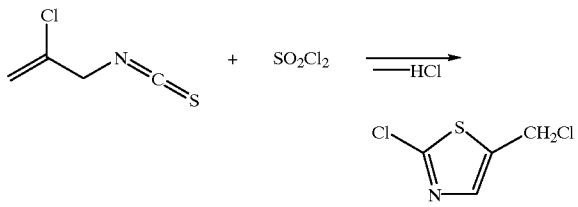

The process according to the present invention can be performed, for example, under the following conditions.

The reaction may typically be performed at −60 to 60° C., preferably at −10 to 50° C. and more preferably at 10 to 40° C. though a wide range of temperature may be selected.

The reaction may preferably be performed under atmospheric pressure though reduced, atmospheric or pressurized pressure may be used.

The reaction may typically be performed for from 10 minutes to 50 hours and preferably for 1 to 20 hours.

After reaction completed, 2-chloro-5-chloromethylthiazole can be isolated by any known methods. For example, reaction mixture may be washed with a suitable amount of water, oil layer may be separated and collected, and then the "aromatic hydrocarbons which may have one or more substituents" may be removed by, for example, vacuum distillation. The "aromatic hydrocarbons which may have one or more substituents" may be collected for recycling.

Hereinafter, the present invention will be described in more detail with reference to the following examples though they are not intended to limit the scope of the present invention.

EXAMPLE 1

2-chloroallyl isothiocyanate (75 g) was mixed with chlorobenzene (136 mL), heated to 30° C. and added dropwise with sulfuryl chloride (84 g) for 3 hours. After stirring at 30° C. for 2 hours, the reaction mixture was added to water (94 g). Separated chlorobenzene layer was added with water (18 g) followed by aqueous solution of 38% potassium carbonate (48 g), and stirred for 30 minutes. Thereafter, oil layer was separated from aqueous layer. The oil layer was distilled under reduced pressure to collect chlorobenzene. The residue was further distilled under reduced pressure to give 77 g of 2-chloro-5-chloromethylthiazole (purity=80%, yield=75%)

EXAMPLE 2

2-chloroallyl isothiocyanate (86 g) was mixed with chlorobenzene (136 mL), heated to 30° C. and added dropwise with sulfuryl chloride (83 g) for 3 hours. After stirring at room temperature for 15 hours, the reaction mixture was added to water (94 g). Additionally, chlorobenzene (40 mL) was added to the mixture which was then heated to 40° C. and stirred for 1 hour. Thereafter, separated chlorobenzene layer was added with water (18 g) followed by dropwise aqueous solution of 38% potassium carbonate (75 g) and stirred for 30 minutes, and oil phase was then separated from aqueous layer. The oil layer was enriched under reduced pressure to collect chlorobenzene. The enriched residue was further distilled under reduced pressure to give 75 g of 2-chloro-5-chloromethylthiazole (purity=95%, yield=76%)

EXAMPLE 3

2-chloroallyl isothiocyanate (30 g) was mixed with toluene (40 mL), and added dropwise with sulfuryl chloride (45 g) at room temperature for 1 hour. After stirring at room temperature for 2 hours, deposited crystal was collected by filtration, washed with toluene (40 mL), mixed with water (40 mL), heated to 40° C. and then cooled to room temperature, and added with aqueous solution of 38% potassium carbonate (16 g) to adjust pH to approximately 2. Then, oil layer was separated from aqueous layer. The oil layer was distilled under reduced pressure to give 26.0 g of 2-chloro-5-chloromethylthiazole (purity=95%, yield=73%).

EXAMPLE 4

2-chloroallyl isothiocyanate (30 g) was mixed with toluene (40 mL), and added dropwise with sulfuryl chloride (45 g) at room temperature for 1 hour. After stirring at room temperature for 2 hours, the mixture was heated to 40° C., stirred for 1 hour, and then added dropwise with water (5 mL). Then, aqueous solution of 38% potassium carbonate (16 g) was added at room temperature to adjust pH to approximately 2. Then, water (10 mL) was added and separated. Toluene layer was enriched under reduced pressure to collect toluene (80%) and then the enriched residue was further distilled under reduced pressure to give 27.1 g of 2-chloro-5-chloromethylthiazole (purity=98.0%, yield=79%)

EXAMPLE 5

2-chloroallyl isothiocyanate (purity=95.5%, 94.2 kg) was mixed with chlorobenzene (181.8 kg), heated to 30° C. and added dropwise with sulfuryl chloride (101.3 kg) for 4 hours. After stirring at 30° C. overnight, the reaction mixture was added to water (113.6 kg). Separated chlorobenzene layer was added with water (22.2 kg) followed by aqueous solution of 38% potassium carbonate (39.1 kg), stirred for 1 hour, and allowed to stand overnight. Thereafter, organic layer was separated from aqueous layer. The organic layer was distilled under reduced pressure to collect chlorobenzene. The residue was further distilled under reduced pressure (102–104° C./16–14 mmHg) to give 87.4 kg of 2-chloro-5-chloromethylthiazole (purity=97.4%, yield=75.2%).

EXAMPLE 6

2-chloroallyl isothiocyanate (purity=94.3%, 1740 kg) was mixed with toluene (1958 kg), heated to 30° C. and added dropwise with sulfuryl chloride (1892 kg) for 4 hours. After stirring at 40° C. for 2 hours, the mixture was added with water (1538 kg) followed by aqueous solution of 38% potassium carbonate (2393 kg), and stirred for 30 minutes, and oil layer was then separated from aqueous layer. The oil layer was enriched under reduced pressure to collect toluene. The enriched residue was further distilled under reduced pressure (86–90° C./4–2 mmHg) to give 1692 kg of 2-chloro-5-chloromethylthiazole (purity=95.0%, yield=77.9%).

As described above, a novel process for preparing 2-chloro-5-chloromethylthiazole is provided according to the present invention in which an excess amount of chlorinating agent is not required, moderate conditions can be used to give a high yield, and solvent can be collected easily after reaction completed.

What is claimed is:

1. A process for preparing 2-chloro-5-chloromethylthiazole of the following formula (I):

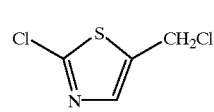

(I)

by allowing 2-halogeno-allyl isothiocyanate of the following formula (II):

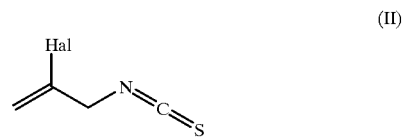

(II)

(wherein Hal represents chlorine or bromine) to react with chlorinating agent in the presence of an aromatic hydrocarbon which may have one or more substituents.

2. The process according to claim 1 wherein the aromatic hydrocarbon which may have one or more substituents is toluene, chlorobenzene or dichlorobenzene.

3. The process according to claim 1 wherein the aromatic hydrocarbon which may have one or more substituents is toluene.

4. The process according to claim 1 wherein Hal in the formula (II) is chlorine.

* * * * *